(12) United States Patent
Kawanobe et al.

(10) Patent No.: US 6,452,056 B1
(45) Date of Patent: Sep. 17, 2002

(54) PROCESS FOR THE PREPARATION OF FLUOROBENZYL DERIVATIVES

(75) Inventors: Tsuneo Kawanobe; Osamu Takazawa, both of Yokohama; Keisuke Yoshikawa, Tokyo; Hiroyuki Watanabe, Kawasaki, all of (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 09/763,130

(22) PCT Filed: Sep. 13, 1999

(86) PCT No.: PCT/JP99/04982

§ 371 (c)(1),
(2), (4) Date: Feb. 20, 2001

(87) PCT Pub. No.: WO00/17138

PCT Pub. Date: Mar. 30, 2000

(30) Foreign Application Priority Data

Sep. 17, 1998 (JP) .............................................. 10-263748

(51) Int. Cl.$^7$ ................................................ C07C 27/10
(52) U.S. Cl. ...................... 568/700; 568/411; 568/425; 568/812; 568/768; 560/226; 560/227; 560/229; 560/254
(58) Field of Search ................................. 568/700, 768, 568/812; 558/411, 425; 560/226, 227, 228, 229, 254

(56) References Cited

FOREIGN PATENT DOCUMENTS

| HU | 195176 B | * | 5/1986 |
| HU | P9902729 A | * | 10/1999 |
| JP | 7-138209 A | * | 6/1995 |

OTHER PUBLICATIONS

Metcalf et al, J. Proc. Natl Sci. 1986, vol. 83, pp. 1549–1553.*
Wade L. G. Organic Chemistry, Third Edition, 1995.*
The Aldrich Catalog, Handbook of Fine Chemicals, 1996–1997.*

* cited by examiner

*Primary Examiner*—Paul J. Killos
*Assistant Examiner*—Héctor Reyes
(74) *Attorney, Agent, or Firm*—Oblon, Spivak, McClelland, Maier & Neustadt, P.C.

(57) ABSTRACT

A fluorine-containing benzonitrile derivative (formula 1) is subjected to a reduction reaction to obtain a fluorine-containing benzylamine derivative (formula 2), and the amino group in said fluorine-containing benzylamine derivative is replaced with a hydroxyl group to obtain a fluorine-containing benzyl alcohol derivative (formula 3):

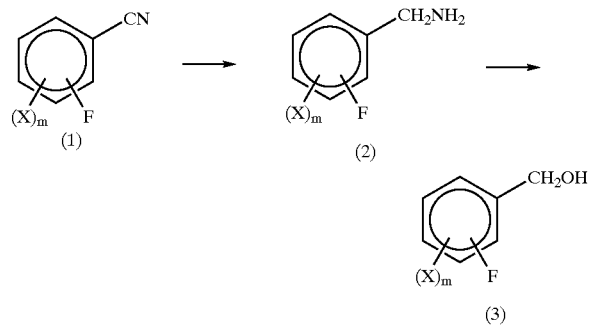

wherein X is a halogen atom, when m is an integer of 2 or more, each X may be the same or different, and m is an integer of from 0 to 4.

8 Claims, No Drawings

PROCESS FOR THE PREPARATION OF FLUOROBENZYL DERIVATIVES

BACKGROUND OF THE INVENTION

1. Field of the Invention

The present invention relates to a process for producing fluorine-containing benzyl derivatives useful as synthesis intermediates for pharmaceutical drugs and agricultural chemicals. Particularly, the present invention provides a novel production process to produce a fluorine-containing benzylamine derivative, a fluorine-containing benzyl alcohol derivative and a fluorine-containing benzyl ester derivative, with a high purity and a high yield, under industrially advantageous operation conditions in short steps. The present invention further provides a novel fluorine-containing benzyl ester derivative useful as an intermediate for pharmaceutical drugs and agricultural chemicals.

2. Background Art

Heretofore, as a process for producing benzyl alcohol employing benzonitrile as a starting material, the following processes have been disclosed:

(1) A process to obtain benzyl alcohol by converting the nitrile group to a carboxylic acid group, followed by a reduction reaction by using lithium aluminum hydride as a reducing agent.

(2) A process to obtain benzyl alcohol, by converting the nitrile group to a formyl group, followed by reduction.

Further, as a process for producing a benzylamine derivative by reducing a benzonitrile derivative, the following processes have been disclosed:

(3) A process for reducing 2-methylbenzonitrile by lithium aluminum hydride (J. Am. Chem. Soc., Vol. 70, 3738 (1948)).

(4) A process for reducing benzonitrile with sodium borohydride and aluminum chloride (J. Am. Chem. Soc., Vol. 78, 2582 (1956))

(5) A process for reducing m-nitrobenzonitrile with sodium borohydride and boron trifluoride (J. Am. Chem. Soc., Vol. 82, 681 (1960)).

(6) A process to obtain 2,6-difluorobenzylamine, by reacting 2,6-difluorobenzonitrile by using sodium borohydride and dimethyl sulfate in tetrahydrofuran (JP-A-7-53476).

However, in the above-mentioned processes, the following problems have been confirmed.

Lithium aluminum hydride to be used in the processes (1) and (3) is inflammable, its handling is thereby difficult, and it is not suitable for an industrial production with a large capacity. In the process (2), the yield of benzaldehyde is poor, whereby there is a problem to employ the process as an industrial production method. Boron trifluoride to be used in the process (5) and dimethyl sulfate to be used in the process (6) are difficult to handle, whereby they are not suitable for an industrial production with a large capacity. Further, sodium borohydride to be used as a reducing agent in the processes (4), (5) and (6), is relatively expensive, and such is economically disadvantageous for the industrial application. Further, in said processes, a large amount of boron compounds which will be industrial waste, will form due to the reaction, such being problematic.

DISCLOSURE OF THE INVENTION

The present inventors have conducted extensive studies to overcome the above-mentioned problems, and as a result, they have found a novel production route and production process to produce a fluorine-containing benzylamine derivative, a fluorine-containing benzyl alcohol derivative and a fluorine-containing benzyl ester derivative, in short steps with a high yield and with a high purity. Further, the present inventors have found a novel compound as an intermediate for pharmaceutical drugs and agricultural chemicals.

Namely, the present invention provides a process for producing a fluorine-containing benzyl alcohol derivative represented by the following general formula (3), which comprises subjecting a fluorine-containing benzonitrile derivative represented by the following general formula (1) to a reduction reaction to obtain a fluorine-containing benzylamine derivative represented by the following general formula (2), and replacing the amino group in said fluorine-containing benzylamine derivative with a hydroxyl group:

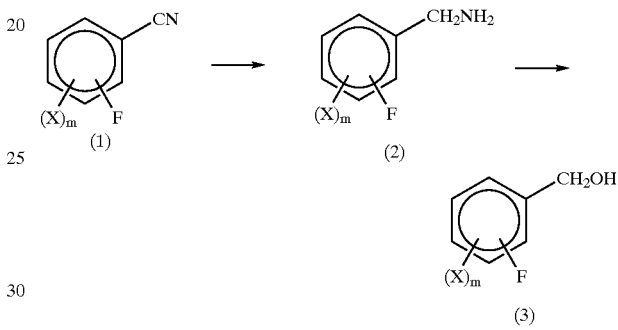

wherein X is a halogen atom, when m is an integer of 2 or more, each X may be the same or different, and m is an integer of from 0 to 4.

Further, the present invention provides a process for producing a fluorine-containing benzyl ester derivative represented by the following general formula (5) and a fluorine-containing benzyl alcohol derivative represented by the following general formula (3), which comprises subjecting a fluorine-containing benzonitrile derivative represented by the following general formula (1) to a reduction reaction to obtain a fluorine-containing benzylamine derivative represented by the following general formula (2), and reacting said fluorine-containing benzylamine derivative with a carboxylic acid compound represented by the following general formula (4) and an alkali nitrite:

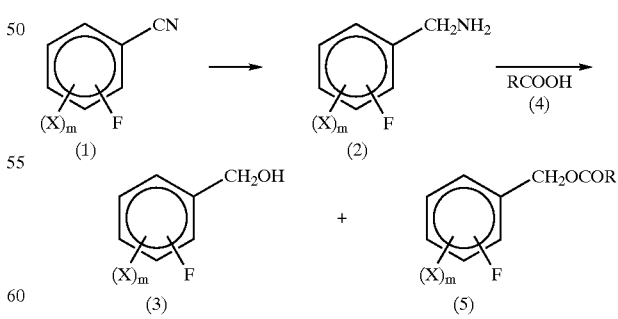

wherein X is a halogen atom, when m is an integer of 2 or more, each X may be the same or different, m is an integer of from 0 to 4, and R is a linear alkyl group which may have a substituent, or a branched alkyl group which may have a substituent.

Still further, the present invention provides a 2,6-difluorobenzyl ester represented by the following general formula (5A):

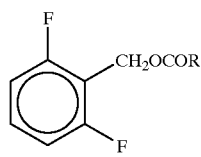

(5A)

wherein R is a linear alkyl group which may have a substituent, or a branched alkyl group which may have a substituent.

In the present specification, the fluorine-containing benzonitrile derivative represented by the general formula (1), the fluorine-containing benzylamine derivative represented by the general formula (2), the fluorine-containing benzyl alcohol represented by the general formula (3), the carboxylic acid compound represented by the general formula (4) and the fluorine-containing benzyl ester derivative represented by the general formula (5) are referred to as compound (1), compound (2), compound (3), compound (4) and compound (5), respectively.

The compound (1) is commercially available, and it is a compound readily available. X in the compound (1) is a halogen atom, and the bonding position is not limited. As said halogen atom, a fluorine atom, a chlorine atom or a bromine atom may be mentioned, and a fluorine atom is preferred.

In the compound (1), m represents the number of X, and is an integer of from 0 to 4. When m is 0, no X is present. Further, when m is an integer of 2 or more, each X may be the same or different. The structure of the compound (1) may optionally be changed depending upon the structure of the desired compound. As the compound (1), a commercially available one as a reagent, or one available for industrial use, can directly be used, and the purity is not particularly limited.

As specific examples of the compound (1), the following compounds may be mentioned.

2-fluorobenzonitrile, 2,3-difluorobenzonitrile, 2,4-difluorobenzonitrile, 2,5-difluorobenzonitrile, 2,6-difluorobenzonitrile, 2,3,4-trifluorobenzonitrile, 2,3,5-trifluorobenzonitrile, 2,3,6-trifluorobenzonitrile, 2,4,5-trifluorobenzonitrile, 2,4,6-trifluorobenzonitrile, 2,3,4,5-tetrafluorobenzonitrile, 2,3,4,5,6-pentafluorobenzonitrile, 3-fluorobenzonitrile, 3,4-difluorobenzonitrile, 3,5-difluorobenzonitrile, 3,4,5-trifluorobenzonitrile, 4-fluorobenzonitrile, 3-chloro-2-fluorobenzonitrile, 4-chloro-2-fluorobenzonitrile, 5-chloro-2-fluorobenzonitrile, 2-chloro-6-fluorobenzonitrile, 3-bromo-2-fluorobenzonitrile, 4-bromo-2-fluorobenzonitrile, 5-bromo-2-fluorobenzonitrile, 2-bromo-6-flubrobenzonitrile, 3,4-dichloro-2,6-difluorobenzonitrile, etc.

As the compound (1), in view of usefulness of the desired compound, reactivity or the like, a compound represented by the following general formula (6) wherein a fluorine atom is attached to the 2-position and a halogen atom ($X^1$) is attached to the 6-position:

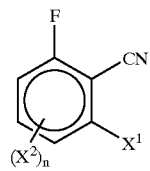

(6)

wherein each of $X^1$ and $X^2$ which are the same or different is a halogen atom, provided that when n is 2 or 3 in the compound (6), the plurality of $X^2$ may be the same or different, and n is an integer of from 0 to 3.

As specific examples of the compound (6), the following compounds may be mentioned.

2,6-difluorobenzonitrile, 2,3,6-trifluorobenzonitrile, 2,4,6-trifluorobenzonitrile, 2,3,4,5,6-pentafluorobenzonitrile, 2-chloro-6-fluorobenzonitrile, 2-bromo-6-fluorobenzonitrile, 3,4-dichloro-2,6-difluorobenzonitrile, etc.

In the present invention, the compound (1) is subjected to a reduction reaction to obtain the compound (2), and the amino group in said compound (2) is replaced with a hydroxyl group to obtain the compound (3). Said production route is a novel production route as a production route of a fluorine-containing benzyl alcohol derivative, and is a short and effective route.

As a method of the reduction reaction wherein the compound (1) is reduced to obtain the compound (2), a conventionally known reduction method may be employed. A hydrogen reduction is preferred, and a method wherein the compound (1) is reduced by hydrogen in the presence of a Raney nickel catalyst or a Raney cobalt catalyst in a non-polar solvent, is particularly preferred.

As the non-polar solvent, pentane, hexane, heptane, cyclohexane, benzene or toluene is preferred. The non-polar solvent may be used alone or as a mixed solvent of two or more of them. The amount of the non-polar solvent is preferably from 0.5 to 10 times, particularly preferably from 1 to 5 times, to the compound (1). If the amount of the non-polar solvent is less than 0.5 time, it is a fear that the yield tends to decrease, and if it exceeds 10 times, the reaction will no longer be advantageous, and such is industrially unfavorable. In the reduction reaction in the present invention, it is particularly preferred to use the non-polar solvent together with a certain reduction catalyst, as the yield will significantly be high. In the case where a polar solvent such as methanol, ethanol, ethyl acetate or dioxane is used instead of said non-polar solvent, the yield of the compound (2) tends to be low.

With respect to a Raney nickel catalyst (hereinafter referred to simply as Ra—Ni) or the Raney cobalt catalyst (hereinafter referred to simply as Ra—Co), a commercial product can directly be used, or it may be preliminarily washed with a solvent such as methanol or ethanol. The amount of the catalyst is preferably from 0.01 to 100 wt %, particularly preferably from 0.1 to 10 wt %, to the compound (1).

The pressure in the reduction reaction is preferably an elevated pressure. For example, it is preferred to make the hydrogen pressure (gage pressure) at least 10 kg/cm² by using a pressure device such as an autoclave, and it is particularly preferred to make the hydrogen pressure from 20 to 100 kg/cm². If the hydrogen pressure is lower than 10 kg/cm², there is a fear that the progress of the reaction is slow and the yield will decrease. The reaction temperature of the reduction reaction is preferably from 80° C. to 170° C., particularly preferably from 100° C. to 150° C. If the reaction temperature is lower than 80° C., there is a fear that the reaction is slow, thus leading to a low yield. On the contrary, at a reaction temperature of at least 170° C., a side-reaction is likely to take place, whereby the purity may decrease. The reaction time is preferably from 1 to 5 hours.

In the present invention, by the reduction reaction of the compound (1), the compound (2) will form. The crude reaction product produced by the reduction reaction may directly be used for the successive reaction. However, it is preferably purified by a conventional after-treatment method for the successive reaction. For example, in the case where the reduction reaction is carried out by a reaction with hydrogen in the presence of Ra—Ni or Ra—Co in the non-polar solvent, it is preferred that the catalyst is separated off from the crude reaction product by filtration, and the non-polar solvent is recovered, followed by distillation under reduced pressure of at a level of from 200 mmHg to 0.01 mmHg, to purify the compound (2).

The compound (2) obtained by the reduction reaction, is a compound having the same structure as the compound (1) except —$CH_2NH_2$. Namely, in the compound (2), each of X and m is the same in the compound (1), and the preferred mode is also the same. Further, the bonding position of each of X and F which bond to the benzene ring, is also the same in the compound (1).

As specific examples of the compound (2), the following compounds may be mentioned.

2-fluorobenzylamine, 2,3-difluorobenzylamine, 2,4-difluorobenzylamine, 2,5-difluorobenzylamine, 2,6-difluorobenzylamine, 2,3,4-trifluorobenzylamine, 2,3,5-trifluorobenzylamine, 2,3,6-trifluorobenzylamine, 2,4,5-trifluorobenzylamine, 2,4,6-trifluorobenzylamine, 2,3,4,5-tetrafluorobenzylamine, 2,3,4,5,6-pentafluorobenzylamine, 3-fluorobenzylamine, 3,4-difluorobenzylamine, 3,5-difluorobenzylamine, 3,4,5-trifluorobenzylamine, 4-fluorobenzylamine, 3-chloro-2-fluorobenzylamine, 4-chloro-2-fluorobenzylamine, 5-chloro-2-fluorobenzylamine, 2-chloro-6-fluorobenzylamine, 3-bromo-2-fluorobenzylamine, 4-bromo-2-fluorobenzylamine, 5-bromo-2-fluorobenzylamine, 2-bromo-6-fluorobenzylamine, 3,4-dichloro-2,6-difluorobenzylamine, etc.

As the compound (2), preferred is a compound represented by the following general formula (7) produced by the reduction reaction of the above-mentioned compound (6):

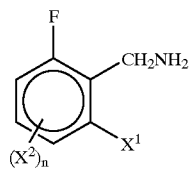

(7)

wherein each of $X^1$, $X^2$ and n is as defined for the compound (6).

As specific examples of the compound (7), the following compounds may be mentioned.

2,6-difluorobenzylamine, 2,3,6-trifluorobenzylamine, 2,4,6-trifluorobenzylamine, 2,3,4,5,6-pentafluorobenzylamine, 2-chloro-6-fluorobenzylamine, 2-bromo-6-fluorobenzylamine, 3,4-dichloro-2,6-difluorobenzylamine, etc.

Then, in the present invention, the amino group in the compound (2) is replaced with a hydroxyl group to obtain the compound (3). The compound (3) is a compound having the same structure as the compound (2) except —$CH_2OH$. Namely, in the compound (3), each of X and n is the same in the compound (2), and the preferred mode is also the same. Further, the bonding position of each of X and F which bond to the benzene ring, is also the same in the compound (2).

As a method to replace the amino group in the compound (2) with a hydroxyl group, the following method may be employed.

Process 1: a process wherein the compound (2) is converted to a tertiary amine compound, ethyl bromide is reacted therewith, and sodium acetate is reacted therewith under an alkali condition in a methanol solvent.

Process 2: a process wherein the compound (2) is reacted with 2,4,5-triphenylpyrylium tetrafluoroborate salt and sodium (2-hydroxymethyl)benzoate in the presence of a phase transfer catalyst.

Process 3: a process to react the compound (2) with an acid and an alkali nitrite.

Process 4: a process wherein a reaction is carried out in the same manner as in Process 3, employing a carboxylic acid compound [following compound (4)] as the acid, and the obtained reaction product is hydrolyzed.

Process 1 is a known process for similar compound (Org. Synth. Coll., vol. 4, 582), and the operations and the conditions of said process can be employed. Further, Process 2 is also a known process for a similar compound (J. Chem. Soc., Perkin Trans. I, 1981, 1492), and the operations and the conditions of said process can be employed.

Process 3 and Process 4 are most preferred processes among the processes to replace the amino group in the compound (2) with a hydroxyl group, in view of yield, economical feasibility, reaction operation and the like. As the alkali nitrite in Process 3 and Process 4, sodium nitrite and potassium nitrite are preferred. The amount of the alkali nitrite is preferably from 1 to 3 equivalent, particularly preferably from 1 to 1.5 equivalent, to the compound (2).

As the acid in Process 3, an inorganic acid or an organic acid is preferred. As the inorganic acid, e.g. sulfuric acid, nitric acid or phosphoric acid is preferred, and sulfuric acid is particularly preferred. The inorganic acid is usually preferably used as an aqueous solution. In the case of an aqueous solution of an inorganic acid, the concentration of the inorganic acid is preferably from 0.01 to 50 wt % in the aqueous solution. The amount of the inorganic acid is preferably from 1 to 10 equivalent, particularly preferably from 1.5 to 5 equivalent, to the compound (2).

In the case of using an organic acid in Process 3, as said organic acid, the carboxylic acid compound [compound (4)] in Process 4 is preferred. The process employing the compound (4) is advantageous as compared with the inorganic acid in view of reaction conditions and reaction operations, and is preferred as an industrial production process. The amount of the carboxylic acid compound is preferably from 1 to 10 equivalent, particularly preferably from 1.5 to 5 equivalent, to the compound (2), in each of Process 3 and Process 4.

In Process 3 and Process 4, the reaction temperature of the compound (2) with the acid (the compound (4) in Process 4) and the alkali nitrite, is preferably from 0 to 80° C., particularly preferably from 10 to 30° C. The reaction time of said reaction is preferably from 0.1 to 48 hours. In Process 3 and Process 4, the addition of the alkali nitrite is preferably carried out by adjusting the compound (2) and the acid such as the compound (4) to be the above-mentioned reaction temperature, and adding the alkali nitrite thereto, while keeping said temperature. The alkali nitrite may be added directly to the reaction system, or its aqueous solution may be added to the reaction system. The aqueous solution is preferred in view of operational efficiency. Further, it is preferred to slowly add the alkali nitrite over a period of from 1 to 5 hours.

The mechanism of the reaction under such a reaction condition that the compound (2), the alkali nitrite and the acid such as the compound (4) are present, is considered to be as follows. Namely, nitrous acid produced by the reaction of the acid and the alkali nitrite, reacts with the amino group of the compound (2), and said amino group is diazotized. By bonding to a hydroxyl group derived from water along with the denitrogen reaction, the amino group is replaced with a hydroxyl group. Although water is involved with said reaction, water may intentionally be added to the reaction system, or may not be added. This is because theoretically equimol of water will be generated at the diazotization. Accordingly, water may not intentionally be added. Further, by water contained in the reaction reagent, or by employing an aqueous solution of the acid or the alkali nitrite, a water-containing reaction can be carried out without intentionally adding water. In the case where the reaction is carried out by intentionally adding water, i.e. in the case where the reaction is carried out by using the compound (2), the acid, the alkali nitrite and water, the amount of water is preferably from 1 to 1,000 wt % to the compound (2).

In the case of using an inorganic acid as the acid in Process 3, usually the compound (3) can be obtained as a product. In the case of using the compound (4) as the acid in Process 3, in an ordinary case, a mixture of the compound (3) with a compound (5) as mentioned hereinafter, can be obtained as a product. This is considered to be attributable to the fact that the compound (2) is diazotized by an effect of the acid such as the compound (4), the compound (4) undergoes the substitution reaction on the carbon atom to which said diazo group is bonded, whereby the compound (5) is produced. The proportion of the compound (3) produced in the mixture of the compound (3) with the compound (5), varies depending upon the amount of water. The proportion of the compound (3) tends to be high with the increase in the amount of water. The compound (3) can be separated off from the mixture of the compound (3) with the compound (5).

In the case where it is intended to obtain the compound (3) with a high yield and a high purity by using the compound (4) as the acid in Process 3, it is preferred to employ Process 4. Namely, it is preferred to react the compound (2) with the compound (4) and the alkali nitrite to obtain a reaction product containing the compound (3) and the compound (5), and to hydrolyze said reaction product. The compound (5) obtained in Process 4, may be separated off from the compound (3), and then hydrolyzed. However, it is effective to hydrolyze the mixture of the compound (3) with the compound (5), and such is preferred. Said hydrolysis reaction can readily be carried out by using the same reaction container.

The hydrolysis reaction in Process 4 is preferably carried out by using an aqueous alkali solution. As the aqueous alkali solution, an aqueous sodium hydroxide solution or an aqueous potassium hydroxide solution is preferred. The reaction time of the hydrolysis reaction is preferably from 10 minutes to 5 hours, particularly preferably from 30 minutes to 1 hour. The hydrolysis is preferably carried out under a heating condition, and the reaction temperature is preferably from 0 to 100° C.

It is preferred to purify the compound (3) produced by the hydrolysis reaction in Process 4, by a conventional after-treatment. As the purification method, a method may be mentioned wherein the crude reaction solution after the completion of the hydrolysis is extracted with the organic layer, followed by distillation under reduced pressure of at a level of from 200 mmHg to 0.01 mmHg.

As specific examples of the compound (3), the following compounds may be mentioned.

2-fluorobenzyl alcohol, 2,3-difluorobenzyl alcohol, 2,4-difluorobenzyl alcohol, 2,5-difluorobenzyl alcohol, 2,6-difluorobenzyl alcohol, 2,3,4-trifluorobenzyl alcohol, 2,3,5-trifluorobenzyl alcohol, 2,3,6-trifluorobenzyl alcohol, 2,4,5-trifluorobenzyl alcohol, 2,4,6-trifluorobenzyl alcohol, 2,3,4,5-tetrafluorobenzyl alcohol, 2,3,4,5,6-pentafluorobenzyl alcohol, 3-fluorobenzyl alcohol, 3,4-difluorobenzyl alcohol, 3,5-difluorobenzyl alcohol, 3,4,5-trifluorobenzyl alcohol, 4-fluorobenzyl alcohol, 3-chloro-2-fluorobenzyl alcohol, 4-chloro-2-fluorobenzyl alcohol, 5-chloro-2-fluorobenzyl alcohol, 2-chloro-6-fluorobenzyl alcohol, 3-bromo-2-fluorobenzyl alcohol, 4-bromo-2-fluorobenzyl alcohol, 5-bromo-2-fluorobenzyl alcohol, 2-bromo-6-fluorobenzyl alcohol, 3,4-dichloro-2,6-difluorobenzyl alcohol, etc.

As the compound (3), preferred is a compound (8) having the amino group in the compound (7) replaced with a hydroxyl group:

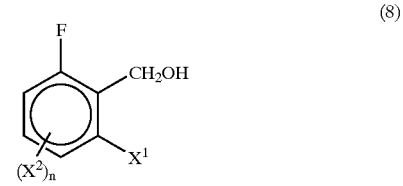

(8)

wherein symbols are as defined for the compound (7).

As specific examples of the compound (8), the following compounds may be mentioned.

2,6-difluorobenzyl alcohol, 2,3,6-trifluorobenzyl alcohol, 2,4,6-trifluorobenzyl alcohol, 2,3,4,5,6-pentafluorobenzyl alcohol, 2-chloro-6-fluorobenzyl alcohol, 2-bromo-6-fluorobenzyl alcohol, 3,4-dichloro-2,6-difluorobenzyl alcohol, etc.

The compound (3) in the present invention is a compound useful as an intermediate for pharmaceutical drugs or agricultural chemicals.

Further, the above-mentioned Process 4 is also a process for synthesizing the compound (5) from the compound (2). Namely, Process 4 is a process for producing the compound (3) and the compound (5) by reacting the compound (2) with the compound (4) and the alkali nitrite:

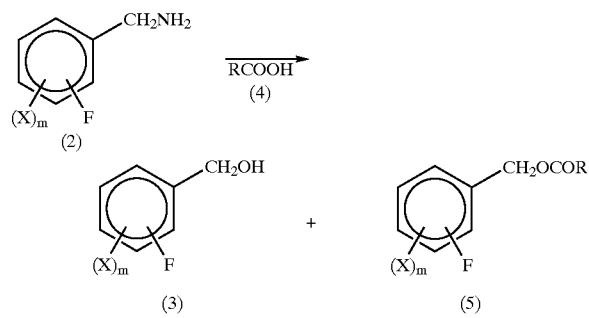

wherein X is a halogen atom, when m is an integer of 2 or more, each X may be the same or different, m is an integer of from 0 to 4, and R is a linear alkyl group which may have a substituent, or a branched alkyl group which may have a substituent.

In the case where R in the compound (4) is a linear alkyl group which have a substituent, a benzyl group, a 2-phenylethyl group or a 3-(2-thiophenyl)propyl group may, for example, be mentioned. In the case where R is an unsubstituted linear alkyl group, a $C_{1-6}$ linear alkyl group is preferred, and a methyl group, an ethyl group, a n-propyl group and a n-butyl group are particularly preferred. In the case where R is a branched alkyl group which have a substituent, a 1-methyl-2-phenylethyl group, a 1-methyl-2-(2-thiophenyl)ethyl group may, for example, be mentioned. In the case where R is an unsubstituted branched alkyl group, a $C_{1-6}$ branched alkyl group is preferred, and an isopropyl group and an isobutyl group are particularly preferred. It is considered that the compound (4) acts also as a reaction solvent in said reaction.

As R in the compound (4), a $C_{1-6}$ linear alkyl group or a $C_{1-6}$ branched alkyl group is preferred. Namely, as the compound (4), a fatty acid containing a lower linear alkyl group or a lower branched alkyl group is preferred, and acetic acid, propionic acid, butyric acid (butanoic acid), isobutyric acid (2-methylpropanoic acid), valeric acid (pentanoic acid), isovaleric acid (3-metylbutanoic acid) and hexanoic acid are preferred.

For the reaction of the compound (2) with the compound (4) and the alkali nitrite in Process 4, the same reaction conditions for the above-mentioned Process 3 can be employed. The proportion of the compound (5) in the reaction product tends to be high with the decrease of the amount of water in the reaction system. Accordingly, in the case where the compound (5) is the desired compound of said reaction, it is preferred to carry out the reaction under a condition that substantially no water is present. However, as mentioned above, in said reaction, water will be generated by the reaction even if water is not added, and the water will produce the compound (3). Accordingly, when it is intended to obtain the compound (5) with a high purity, it is preferred to carry out a conventional separation method. Further, the mixture of the compound (3) with the compound (5) may directly undergo esterification. Said esterification reaction can readily be carried out by using the same reaction container under a condition that no water is added.

The compound (5) is a novel compound. As the compound (5), acetate, propionate, butyrate, isobutyrate, valerate, isovalerate or hexanoate, of the above-mentioned compound (3), may, for example, be mentioned.

As the compound (5), a 2,6-difluorobenzyl ester, a 2,3,6-trifluorobenzyl ester, a 2,4,6-trifluorobenzyl ester, a 2,3,4,5,6-pentafluorobenzyl ester, a 2-chloro-6-fluorobenzyl ester, a 2-bromo-6-fluorobenzyl ester or a 3,4-dichloro-2,6-difluorobenzyl ester may be mentioned. Among such compounds (5), a 2,6-difluorobenzyl ester wherein 2,6-positions of the benzene ring is replaced with fluorine, is particularly preferred. As specific examples of said compounds, 2,6-difluorobenzyl acetate, 2,6-difluorobenzyl propionate, 2,6-difluorobenzyl butyrate, 2,6-difluorobenzyl isobutyrate, 2,6-difluorobenzyl valerate, 2,6-difluorobenzyl isovalerate and 2,6-difluorobenzyl hexanoate may, for example, be mentioned.

The compound (5) itself is a compound useful as an intermediate for pharmaceutical drugs and agricultural chemicals. Further, it is also a useful compound since said compound can be hydrolyzed to produce the compound (3) useful as an intermediate for pharmaceutical drugs and agricultural chemicals.

By the process of the present invention, a fluorine-containing benzyl alcohol derivative and a fluorine-containing benzyl ester derivative, useful as synthesis intermediates for pharmaceutical drugs and agricultural chemicals, can be produced industrially advantageously.

Now, the present invention will be explained in detail with reference to Examples and Comparative Examples. However, the present invention is by no means restricted thereto. J in Examples represents spin coupling constant of $^{13}C$ and $^{19}F$ in $^{13}CNMR$ spectrum.

EXAMPLE 1

Synthesis Example for 2,6-difluorobenzylamine

To an autoclave of 1 l, 150 g of 2,6-difluorobenzonitrile, 150 g of hexane and 7.5 g of Ra—Ni washed with 99% ethanol, were charged, a replacement with nitrogen gas was carried out, and a reaction was carried out at a hydrogen pressure of from 30 to 40 kg/cm$^2$ at a reaction temperature of 130° C. for 2.5 hours. After the completion of the reaction, the reaction mixture was subjected to filtration to separate off the catalyst, and hexane was recovered by distillation, followed by distillation under reduced pressure to obtain 146 g of 2,6-difluorobenzylamine (boiling point: 82° C./25 mmHg) (yield: 94.6%, purity: 99.2%).

EXAMPLES 2 to 4

Synthesis Examples for 2,6-Difluorobenzylamine

The solvent, the catalyst, the reaction temperature and the reaction pressure in Example 1 were changed as shown in Table 1, to produce 2,6-difluorobenzylamine. The yield and the purity are shown in Table 1.

TABLE 1

| Ex. | Non-polar solvent | Catalyst | Reaction temperature | Reaction pressure (kg/cm$^2$) | Yield (%) | Purity (%) |
|---|---|---|---|---|---|---|
| 2 | Cyclohexane | Ra—Ni | 110 | 30–40 | 90.2 | 99.3 |
| 3-1 | Toluene | Ra—Ni | 130 | 30–40 | 91.3 | 99.4 |
| 3-2 | Benzene | Ra—Ni | 130 | 30–40 | 90.0 | 99.1 |
| 4-1 | Hexane | Ra—Co | 150 | 25–40 | 88.0 | 99.0 |
| 4-2 | Pentane | Ra—Co | 150 | 25–40 | 86.1 | 99.0 |
| 4-3 | Heptane | Ra—Co | 150 | 25–40 | 89.0 | 99.2 |

EXAMPLE 5

Synthesis Example for 2,6-Difluorobenzyl Alcohol 75 g of 10% aqueous sulfuric acid solution was charged, and 14.3 g of 2,6-difluorobenzylamine obtained in Example 1 was dropwise added thereto under cooling. Then, under cooling, a solution comprising 10.4 g of sodium nitrite and 20 g of water was dropwise added thereto over a period of 30 minutes at a reaction temperature of from 10 to 20° C. After the completion of the dropwise addition, stirring was carried out at the same temperature for 1 hour. After the completion of the reaction, neutralization in an aqueous sodium hydrogencarbonate solution was carried out, and extraction with methylene chloride was carried out. Methylene chloride was recovered, followed by distillation under reduced pressure to obtain 12.4 g of 2,6-difluorobenzyl alcohol (103° C./26 mmHg) (yield: 86.1%, purity: 88.1%).

EXAMPLE 6

Synthesis Example for 2,6-Difluorobenzyl Alcohol 13.5 g of 2,6-difluorobenzylamine and 11.9 g of water were charged, and 11.9 g of acetic acid was dropwise added thereto gradually under cooling. Then, under cooling, a solution comprising 7.2 g of sodium nitrite and 14 g of water was dropwise added thereto at a reaction temperature of from 10 to 20° C. over a period of 1.5 hours. After the completion of the dropwise addition, stirring was carried out at the same temperature for 1 hour, and the mixture was left at room temperature overnight to obtain a reaction product containing 2,6-difluorobenzyl acetate and 2,6-difluorobenzyl alcohol.

Then, 11.4 g of a 50% aqueous solution of sodium hydroxide was added to this reaction product, followed by stirring at 60° C. for 1 hour to carry out hydrolysis. After the completion of the hydrolysis, the reaction mixture was cooled, and extraction with methylene chloride was carried out. Methylene chloride was recovered, followed by distillation under reduced pressure, to obtain 12.1 g of 2,6-difluorobenzyl alcohol (yield: 89.0%, purity: 99.9%).

EXAMPLE 7

Synthesis Example for 2,6-Difluorobenzyl Alcohol 85.8 g of acetic acid was charged, and 42.9 g of 2,6-difluorobenzylamine was dropwise added thereto gradually under cooling. Then, under cooling, 31.1 g of sodium nitrite was added thereto at a reaction temperature of from 10 to 20° C. over a period of 3.5 hours. After the completion of the addition, stirring was carried out at the same temperature for 1 hour, and the mixture was left at room temperature overnight to obtain a reaction product containing 2,6-difluorobenzyl acetate and 2,6-difluorobenzyl alcohol.

Then, 200 g of a 50% aqueous solution of sodium hydroxide was added to the reaction product, followed by stirring under reflux (80° C.) for 1 hour, to carry out hydrolysis. After the completion of the hydrolysis, the reaction mixture was cooled, and extraction with methylene chloride was carried out. Methylene chloride was recovered, followed by distillation under reduced pressure, to obtain 41.1 g of 2,6-difluorobenzyl alcohol (yield: 95.1%, purity: 99.3%).

EXAMPLES 8 to 32

Synthesis Examples for Fluorine-containing Benzylamine Derivatives

The reaction was carried out in the same manner as in Example 1 by using, instead of 2,6-difluorobenzonitrile in Example 1, the corresponding fluorine-containing benzonitrile derivative. The produced fluorine-containing benzylamine derivatives, and the yield and the purity thereof, are shown in Table 2.

TABLE 2

| Ex. | Fluorine-containing benzylamine derivative | Yield (%) | Purity (%) |
|---|---|---|---|
| 8 | 2-fluorobenzylamine | 95.2 | 99.1 |
| 9 | 2,3-difluorobenzylamine | 94.7 | 99.0 |
| 10 | 2,4-difluorobenzylamine | 93.2 | 99.4 |
| 11 | 2,5-difluorobenzylamine | 94.7 | 99.2 |
| 12 | 2,3,4-trifluorobenzylamine | 90.1 | 99.1 |
| 13 | 2,3,5-trifluorobenzylamine | 89.7 | 99.5 |
| 14 | 2,3,6-trifluorobenzylamine | 90.1 | 99.3 |
| 15 | 2,4,5-trifluorobenzylamine | 88.9 | 99.3 |
| 16 | 2,4,6-trifluorobenzylamine | 89.3 | 99.0 |
| 17 | 2,3,4,5-tetrafluorobenzylamine | 87.3 | 98.9 |
| 18 | 3-fluorobenzylamine | 96.8 | 99.3 |
| 19 | 3,4-difluorobenzylamine | 94.0 | 99.1 |

TABLE 2-continued

| Ex. | Fluorine-containing benzylamine derivative | Yield (%) | Purity (%) |
|---|---|---|---|
| 20 | 3,5-difluorobenzylamine | 95.2 | 99.1 |
| 21 | 3,4,5-trifluorobenzylamine | 90.7 | 99.4 |
| 22 | 4-fluorobenzylamine | 95.9 | 99.1 |
| 23 | 2,3,4,5,6-pentafluorobenzylamine | 80.2 | 99.2 |
| 24 | 3-chloro-2-fluorobenzylamine | 90.1 | 96.6 |
| 25 | 4-chloro-2-fluorobenzylamine | 90.7 | 97.0 |
| 26 | 5-chloro-2-fluorobenzylamine | 91.3 | 95.1 |
| 27 | 2-chloro-6-fluorobenzylamine | 82.7 | 93.5 |
| 28 | 3,4-dichloro-2,6-difluorobenzylamine | 80.7 | 90.3 |
| 29 | 3-bromo-2-fluorobenzylamine | 81.5 | 89.7 |
| 30 | 4-bromo-2-fluorobenzylamine | 82.3 | 90.8 |
| 31 | 5-bromo-2-fluorobenzylamine | 84.4 | 89.3 |
| 32 | 2-bromo-6-fluorobenzylamine | 82.2 | 90.0 |

EXAMPLES 33 to 57

Synthesis Examples for Fluorine-containing Benzyl Alcohol Derivatives

A fluorine-containing benzyl alcohol derivative was produced in the same manner as in Example 6 by using, instead of 2,6-difluorobenzylamine in Example 6, the corresponding fluorine-containing benzylamine derivative. The produced fluorine-containing benzyl alcohol derivatives, and the yield and the purity thereof, are shown in Table 3.

TABLE 3

| Ex. | Fluorine-containing benzyl alcohol derivative | Yield (%) | Purity (%) |
|---|---|---|---|
| 33 | 2-fluorobenzyl alcohol | 90.5 | 99.1 |
| 34 | 2,3-difluorobenzyl alcohol | 89.8 | 99.3 |
| 35 | 2,4-difluorobenzyl alcohol | 89.6 | 99.5 |
| 36 | 2,5-difluorobenzyl alcohol | 91.1 | 99.2 |
| 37 | 2,3,4-trifluorobenzyl alcohol | 86.6 | 99.0 |
| 38 | 2,3,5-trifluorobenzyl alcohol | 85.4 | 99.1 |
| 39 | 2,3,6-trifluorobenzyl alcohol | 85.8 | 99.1 |
| 40 | 2,4,5-trifluorobenzyl alcohol | 84.7 | 99.4 |
| 41 | 2,4,6-trifluorobenzyl alcohol | 88.4 | 99.0 |
| 42 | 2,3,4,5-tetrafluorobenzyl alcohol | 85.1 | 99.3 |
| 43 | 3-fluorobenzyl alcohol | 92.2 | 99.1 |
| 44 | 3,4-difluorobenzyl alcohol | 89.5 | 99.1 |
| 45 | 3,5-difluorobenzyl alcohol | 90.7 | 99.5 |
| 46 | 3,4,5-trifluorobenzyl alcohol | 86.4 | 99.6 |
| 47 | 4-fluorobenzyl alcohol | 91.3 | 99.6 |
| 48 | 2,3,4,5,6-pentafluorobenzyl alcohol | 80.5 | 99.0 |
| 49 | 3-chloro-2-fluorobenzyl alcohol | 85.3 | 94.7 |
| 50 | 4-chloro-2-fluorobenzyl alcohol | 83.2 | 95.1 |
| 51 | 5-chloro-2-fluorobenzyl alcohol | 83.8 | 94.4 |
| 52 | 2-chloro-6-fluorobenzyl alcohol | 82.9 | 95.5 |
| 53 | 3,4-dichloro-2,6-difluorobenzyl alcohol | 81.0 | 90.0 |
| 54 | 3-bromo-2-fluorobenzyl alcohol | 80.1 | 90.7 |
| 55 | 4-bromo-2-fluorobenzyl alcohol | 81.2 | 89.9 |
| 56 | 5-bromo-2-fluorobenzyl alcohol | 82.3 | 90.2 |
| 57 | 2-bromo-6-fluorobenzyl alcohol | 81.5 | 91.1 |

EXAMPLE 58

Synthesis Example for 2,6-difluorobenzyl Acetate

To an autoclave of 1 l, 150 g of 2,6-difluorobenzonitrile, 150 g of hexane and 7.5 g of Ra—Ni were charged, replacement with hydrogen gas was carried out, and a reaction was carried out at a hydrogen pressure of from 30 to 40 kg/cm$^2$ at a reaction temperature of 130° C. for 2.5 hours. After the completion of the reaction, the reaction mixture was subjected to filtration to separate off the catalyst, and hexane was recovered by distillation, followed by distillation under reduced pressure to obtain 146 g of 2,6-difluorobenzylamine (boiling point: 82° C./25 mmHg).

Then, 135 g of the obtained 2,6-difluorobenzylamine was dropwise added gradually to 270 g of acetic acid under cooling with water. Then, under cooling while keeping the reaction temperature to be from 10 to 30° C., 72 g of sodium nitrite was gradually added thereto over a period of 2 hours for reaction. After the completion of the addition, stirring was carried out at the same temperature for 3 hours. After the completion of the reaction, extraction with diethyl ether was carried out, and said extract was washed with aqueous sodium chloride solution and aqueous sodium carbonate solution. Diethyl ether was recovered, followed by distillation under reduced pressure, to obtain 155 g of a mixture comprising 2,6-difluorobenzyl alcohol and 2,6-difluorobenzyl acetate (71–81° C./5 mmHg) (2,6-difluorobenzyl alcohol/2,6-difluorobenzyl acetate=22/78, yield of the mixture: 93.9%).

2,6-difluorobenzyl acetate can readily be isolated from the mixture with a high purity, by means of a precise distillation or silica gel chromatography. By the precise distillation, 109 g (yield: 62.1%, purity: 99.3%) was obtained (boiling point: 81° C./5 mmHg).

Spectrum data of the produced 2,6-difluorobenzyl acetate are shown below.

$^1$H-NMR (CDCl$_3$): δ=2.08 (s, 3H), 5.20 (s, 2H), 6.92 (m, 2H), 7.32 (m, 1H). $^{13}$C-NMR (CDCl$_3$): δ=170.518 (s) 161.855 (d, J=251.4 Hz), 161.781 (d, J=251.5 Hz), 130.748 (t, J=10.8 Hz), 111.825 (t, J=19.0 H z), 111.345 (d, J=19.0 Hz), 111.287 (d, J=19.0 Hz), 53.948 (t, J=4.1 Hz), 20.652 (s). IR (neat): 1745, 1630, 1595, 1473, 1275, 1237, 1060, 1030, 786 cm$^{-1}$.

EXAMPLE 59

Synthesis Example for 2,6-Difluorobenzyl Propionate 2,6-difluorobenzyl propionate was produced from 2,6-difluorobenzonitrile in the same manner as in Example 58 by using propionic acid instead of acetic acid in Example 58 (boiling point: 83° C./3 mmHg, yield: 61.8%, purity: 99.2%).

Spectrum data of the produced 2,6-difluorobenzyl propionate are shown below.

$^1$H-NMR (CDCl$_3$): δ=1.12 (t, 3H), 2.33 (q, 2H), 5.20 (s, 2H), 6.90 (m, 2H), 7.31 (m, 1H). $^{13}$C-NMR (CDCl$_3$): δ=173.414 (s), 161.588 (d, J=250.6 Hz), 161.513 (d, J=250.6 Hz), 130.419 (t, J=10.4 Hz), 111.792 (t, J=19.0 Hz), 110.991 (d, J=19.1 Hz), 110.933 (d, J=19.1 Hz), 53.429 (t, j=4.1 Hz), 26.839 (s), 8.493 (s). IR (neat): 1743, 1630, 1595, 1473, 1275, 1237, 1174, 1059, 786 cm$^{-1}$.

EXAMPLE 60

Synthesis Example for 2,6-Dichlorobenzyl Butyrate 2,6-difluorobenzyl butyrate was produced from 2,6-difluorobenzonitrile in the same manner as in Example 58 by using butyric acid instead of acetic acid in Example 58. Boiling point: 100° C./4 mmHg, yield: 60.7%, purity: 99.3%. Spectrum data of the produced 2,6-difluorobenzyl butyrate are shown below.

$^1$H-NMR (CDCl$_3$): δ=0.92 (t, 3H), 1.64 (m, 2H), 2.29 (t, 2H), 5.20 (s, 2H), 66.90 (m, 2H), 7.31 (m, 1H). $^{13}$C-NMR (CDCl$_3$): δ=172.616 (s), 161.608 (d, J=251.4 Hz), 161.534 (d, J=251.4 Hz), 130.410 (t, J=10.4 Hz), 111.842 (t, J=18.6 Hz), 111.007 (d, J=19.0 Hz), 110.941 (d, J=19.0 Hz), 53.347 (t, J=3.7 Hz), 35.469 (s), 18.044 (s), 13.051 (s). IR (neat): 1741, 1630, 1595, 1473, 1274, 1237, 1172, 1059, 786 cm$^{-1}$.

EXAMPLE 61

Synthesis Example for 2,6-Difluorobenzyl Isobutyrate 2,6-difluorobenzyl isobutyrate was produced from 2,6-difluorobenzonitrile in the same manner as in Example 58 by using isobutyric acid instead of acetic acid in Example 58. Boiling point: 93° C./4 mmHg, yield: 58.1%, purity: 99.1%. Spectrum data of the obtained 2,6-difluorobenzyl isobutyrate are shown below.

$^1$H-NMR (CDCl$_3$): δ=1.15 (d, 6H), 2.55 (m, 1H), 5.20 (s, 2H), 6.90 (m, 2H), 7.31 (m, 1H). $^{13}$C-NMR (CDCl$_3$): δ=176.063 (s), 161.604 (d, J=250.6 Hz), 161.530 (d, J=250.6 Hz), 130.361 (t, J=10.4 Hz), 111.899 (t, J=19.1 Hz), 111.007 (d, J=19.0 Hz), 110.941 (d, J=19.0 Hz), 53.544 (t, J=3.3 Hz), 33.487 (s), 18.390 (s). IR (neat): 1739, 1629, 1595, 1472, 1274, 1237, 1151, 1058, 786 cm$^{-1}$.

EXAMPLE 62

Synthesis Example for 2,6-Difluorobenzyl Valerate 2,6-difluorobenzyl valerate was produced from 2,6-difluorobenzonitrile in the same manner as in Example 58 by using valeric acid instead of acetic acid in Example 58. Boiling point: 102° C./3 mmHg, yield: 57.1%, purity: 99.3%. Spectrum data of the obtained 2,6-difluorobenzyl valerate are shown below.

$^1$H-NMR (CDCl$_3$): δ=0.88 (t, 3H), 1.32 (m, 2H), 1.60 (m, 2H), 2.30 (t, 2H), 5.20 (s, 2H), 6.90 (m, 2H), 7.30 (m, 1H). $^{13}$C-NMR (CDCl$_3$): δ=172.698 (s), 161.588 (d, J=250.6 Hz), 161.509 (d, J=251.5 Hz), 130.369 (t, J=10.8 Hz), 111.825 (t, J=19.0 Hz), 110.966 (d, J=19.0 Hz), 110.900 (d, J=19.1 Hz), 53.322 (t, J=4.2 Hz), 33.273 (s), 26.601 (s), 21.79 (s), 13.125 (s). IR (neat): 1741, 1630, 1595, 1472, 1274, 1237, 1167, 1059, 786 cm$^{-1}$.

According to the production process of the present invention, the compound (2) and the compound (3) can be obtained from the readily available compound (1) without employing a special reaction reagent or reaction condition, with a high yield and a high purity. Further, the compound (5) can also be obtained from the compound (2) without employing a special reaction reagent or reaction condition. The production process of the present invention is an effective process, since the reaction steps are short, and each step can be carried out with a high yield. Further, it is an excellent process which can be employed as an industrial production process with a large capacity.

What is claimed is:

1. A process for producing a fluorine-containing benzyl alcohol derivative represented by the following general formula (3), which comprises subjecting a fluorine-containing benzonitrile derivative represented by the following general formula (1) to a reduction reaction with a reducing agent consisting essentially of hydrogen in the presence of a Raney nickel catalyst or a Raney cobalt catalyst in a non-polar solvent to obtain a fluorine-containing benzylamine derivative represented by the following general formula (2), and replacing the amino group in said fluorine-containing benzylamine derivative with a hydroxyl group by one of the following processes:

Process 1: a process wherein the compound (2) is converted to a tertiary amine compound, ethyl bromide is reacted therewith, and sodium acetate is reacted therewith under an alkali condition in a methanol solvent, Process 2: a process wherein the compound (2) is reacted with 2,4,5-triphenylpyrylium tetrafluoroborate salt and sodium (2-hydroxymethyl)benzoate in the presence of a phase transfer catalyst, Process 3: a process wherein the compound (2) is reacted with an acid and an alkali nitrite, Process 4: a process wherein a reaction is carried out in the same manner as in Process 3, employing a carboxylic acid compound as the acid, and the obtained reaction product is hydrolyzed,

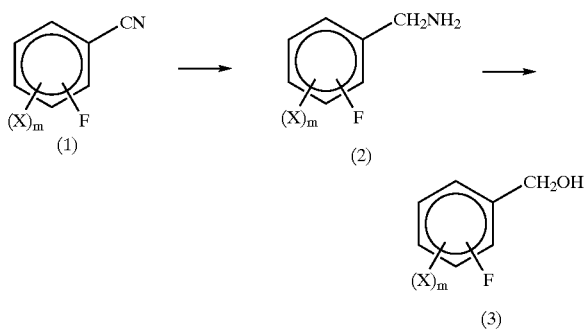

wherein X is a halogen atom, when m is an integer of 2 or more, each X may be the same or different, and m is an integer of from 0 to 4.

2. The process for producing a fluorine-containing benzyl alcohol derivative according to claim 1, which comprises reacting the fluorine-containing benzylamine derivative represented by the general formula (2) with an acid and an alkali nitrite, followed by a hydrolysis as the case requires, to replace the amino group with a hydroxyl group.

3. A process for producing a fluorine-containing benzylamine derivative represented by the following general formula (2), which comprises reacting a fluorine-containing benzonitrile derivative represented by the following general formula (1) with a reducing agent consisting essentially of hydrogen in the presence of a Raney nickel catalyst or a Raney cobalt catalyst in a non-polar solvent:

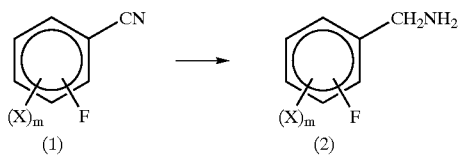

wherein X is halogen atom, when m is an integer of 2 or more, each X may be the same or different, and m is an integer of from 0 to 4.

4. A process for producing a fluorine-containing benzyl alcohol derivative represented by the following general formula (3), which comprises reacting a fluorine-containing benzylamine derivative represented by the following general formula (2) with an acid and an alkali nitrite, followed by hydrolysis as the case requires:

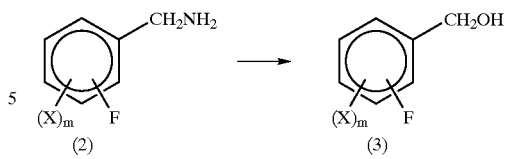

wherein X is a halogen atom, when m is an integer of 2 or more, each X may be the same or different, and m is an integer of from 0 to 4.

5. A process for producing a fluorine-containing benzyl alcohol represented by the following general formula (3) and a fluorine-containing benzyl ester derivative represented by the following general formula (5), which comprises subjecting a fluorine-containing benzonitrile derivative represented by the following general formula (1) to a reduction reaction with a reducing agent consisting essentially of hydrogen in the presence of a Raney nickel catalyst or a Raney cobalt catalyst in a non-polar solvent to obtain a fluorine-containing benzylamine derivative represented by the following general formula (2), and reacting said fluorine-containing benzylamine derivative with a carboxylic acid compound represented by the following general formula (4) and an alkali nitrite:

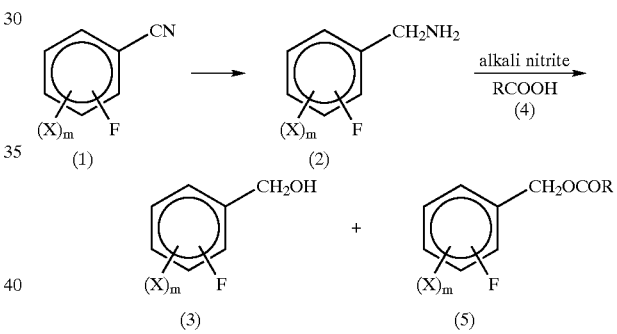

wherein X is a halogen atom, when m is an integer of 2 or more, each X may be the same or different, m is an integer of from 0 to 4, and R is a linear alkyl group which may have a substituent, or a branched alkyl group which may have a substituent.

6. A process for producing a fluorine-containing benzyl alcohol derivative represented by the following general formula (3) and a fluorine-containing benzyl ester derivative represented by the following general formula (5), which comprises reacting a fluorine-containing benzylamine derivative represented by the following general formula (2) with a carboxylic acid compound represented by the following general formula (4) and an alkali nitrite:

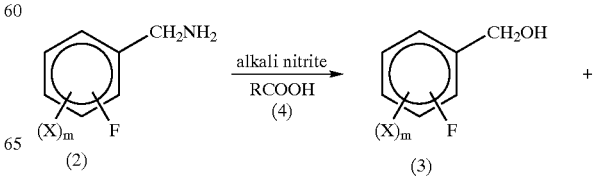

-continued

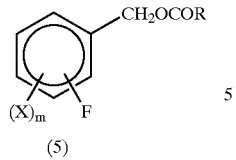

(5)

wherein X is a halogen atom, when m is an integer of 2 or more, each X may be the same or different, m is an integer of from 0 to 4, and R is a linear alkyl group which may have a substituent, or a branched alkyl group which may have a substituent.

7. A process for producing a fluorine-containing benzyl alcohol derivative represented by the following general formula (3), which comprises reacting a fluorine-containing benzylamine derivative represented by the following general formula (2) with a carboxylic acid compound represented by the following general formula (4) and an alkali nitrite, to obtain a reaction product containing the fluorine-containing benzyl alcohol derivative represented by the following general formula (3) and a fluorine-containing benzyl ester derivative represented by the following general formula (5), followed by hydrolysis of said reaction product comprising a benzyl ester derivative represented by the general formula (5):

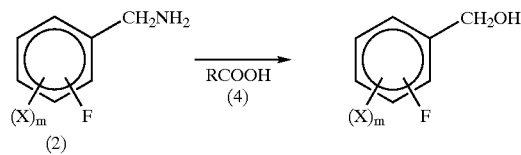

-continued

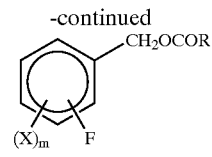

(3)

wherein X is a halogen atom, when m is an integer of 2 or more, each X may be the same or different, m is an integer of from 0 to 4, and R is a linear alkyl group which may have a substituent, or a branched alkyl group which may have a substituent.

8. A 2,6-difluorobenzyl ester derivative represented by the following general formula (5A):

(5A)

wherein R is a linear $C_{2-6}$-alkyl group which may have a substituent, or a branched $C_{2-6}$-alkyl group which may have a substituent.

* * * * *